(12) United States Patent
Liu

(10) Patent No.: US 6,855,353 B2
(45) Date of Patent: Feb. 15, 2005

(54) METHOD FOR PRODUCING ANTIOXIDANT AND PREVENTION OF CANCER

(76) Inventor: Yaguang Liu, 67-08 168th St., Flushing, NY (US) 11365

( * ) Notice: Subject to any disclaimer, the term of this patent is extended or adjusted under 35 U.S.C. 154(b) by 135 days.

(21) Appl. No.: 10/092,638

(22) Filed: Mar. 8, 2002

(65) Prior Publication Data

US 2003/0175372 A1 Sep. 18, 2003

(51) Int. Cl.[7] .......................... A61K 35/78; A61K 31/05

(52) U.S. Cl. ....................... 424/776; 424/725; 424/779; 514/732; 514/734; 514/736

(58) Field of Search ................................. 424/725, 776, 424/779; 514/730, 731, 732, 734, 736

*Primary Examiner*—Christopher R. Tate

(57) ABSTRACT

A pharmaceutical composition for prevention and treatment of cancer, cardiovascular disease and antioxidation contains resveratol. The new method of process for producing resveratol is extracted resveratol from oil residue and stems of peanuts or stems of other cheap herbs. Derivates of resveratol include procyanidins, polydatin, peceid, anthraglycoside, emodin, chrysophanol and quercetin.

1 Claim, No Drawings

METHOD FOR PRODUCING ANTIOXIDANT AND PREVENTION OF CANCER

BACKGROUND OF THE INVENTION

A pharmaceutical composition for prevention and treatment of cancer, cardiovascular disease and antioxidation contains resveratol. The new method of process for producing resveratol is extracted resveratol from oil residue and stems of peanuts or stems of other cheap herbs.

DESCRIPTION OF PRIOR ART

It has demonstrated that resveratol (RES) and its derivatives shown remarkably preventing effect on the development of cancer and cardiovascular disease. But natural source of extracting resveratol is limited in seed and skin of grapes so far. Therefore, the price of resveratol is expensive.

We also found that resveratol is a very strong antioxidant. In fact, disorder of anti-oxidation and peroxidation will cause cardiovascular disease, cancer, alzheimer and other diseases. For example, oxidation of lower density lipoprotein (LDL) is very important in heart disease. Over oxidized LDL involves plaques and clot formation and ischemia occurs in development of atherosclerosis. The results are that more oxidative injury caused in the vascular endothelium.

Hypertension will cause heart disease. One of the reasons is hypertension causes damaging effects of turbulent flow and high pressure on the endothelium and then causes oxidative injury. Together, these forces cause thickening of basement membranes, making for inefficient nutrient and waste exchange. This, in turn, results in formation of scar tissue and a steady loss of organ function. After that oxidative injury of venous caused acceleration of atherosclerotic plaque formation, which impedes perfusion. Plaque material can break off from the vessel walls and occlude the vessel further along as it narrows. Catastrophic rupture of a blood vessel whose wall was weakened by plaque formation and scarring e.g., in the brain, resulting in a stroke.

Obviously, oxidative injury is an important reason for cardiovascular disease and stroke. Over oxidation will induce tumorigenesis at least in skin, colon, forestomach, esophagus and lung. The tumor promoter decreases activity of glutathione peroxidase (GSH-Px) in the chemical carcinogen-induced development of cancer. Antioxidant plays important role against the tumor promoter. The decreasing in the activities of antioxidant and GSH-Px occurs during tumorigenesis.

Alzheimer's disease (AD) is a rapidly progressive dementia disease of elderly patients. AD has focused on abnormal metabolism of the amyloid precursor protein (APP), which in AD appears to generate a cleavage product called β-amyloid peptide. The β-amyloid peptide is a major component of the plaques that are noted throughout the brain of AD patients, along with neurofibrillary tangles and neuronal loss.

A recent paper demonstrates that estrogen reduces the formation of the AD-associated β-amyloid peptide, perhaps by stimulating the intracellular trafficking of APP and thereby diminishing the amount of protein available for conversion to the toxic fragments.

Protection from β-amyloid pathology conferred by estrogen is independent of cells having nuclear estrogen receptors, and thus may not be working trough classical mechanisms of estrogen action. Furthermore, this study identified an important effect of antioxidants in greatly increasing the sensitivity of cells to this estrogen-protective mechanism. Both of these observations have significant potential to contribute to the prevention and perhaps even treatment of this dread disorder. For the reasons given above, the effect of antioxidants is important in development of AD.

DETAILED DESCRIPTION

A pharmaceutical composition for prevention and treatment of cancer, cardiovascular disease and antioxidation contains resveratol. The process for producing RES is extracting resveratol from oil residue of peanuts and stems of peanuts or other cheap herbs. Above process also can produce RES' derivate including procyanidins, polydatin, peceid, anthraglycoside, emodin, chrysophanol and quercetin.

The mail purpose of using peanuts is used for extracting peanuts oil, peanut butter, candy, salted peanuts and other food. Production in the U.S. is ~$1.5 \times 10^6$ metric tons, and the world production is $16-17 \times 10^6$ metric tons. So far, peanut oil residue or stems of peanut, which have a huge amount, are almost a waste. Other side, resveratol is expensive because the source of resveratol from seed or skin of grapes. Therefore, extracting resveratol from peanut oil residue, stems of peanut or cheap herbs is a new and important method. The cheap herbs include plants of Arachis L., Leguminosae L. and Polygonum L. In fact, plant stem of Arachis L and Leguminosae L are agriculture wastage.

For the reason given above, the present invention has a great economic and environmental value.

Resveratol has the following chemical structure

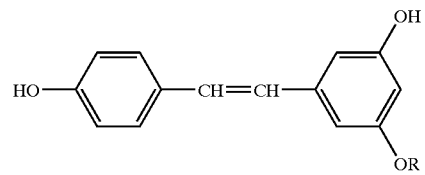

Molecular mp: 256–257° C., crystals

The following specific examples will provide detailed illustrations of methods of producing relative drugs, according to the present invention and pharmaceutical dosage units containing relative drugs. Moreover, examples described pharmaceutical characters of drugs, which demonstrated its effectiveness in control of cancer cells. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Resveratol from Peanut Residue

After peanuts were extracted oil, residue of peanut was solid, which named peanut residue (PR). PR was obtained from factory of manufacturing peanut oil or purchased from market.

One kg of dried powder of PR was extracted by 5L of 95% of ethanol. The powder was recovered by filtration. Filtrate was saved and powder filtercake was refluxed twice with 3 liter of 95% of ethanol on steam bath. Filtrates were combined and distilled at reduced pressure. The ethanol was recovered and the still residue was obtained. The still residue was extracted by 500 ml of water and 500 ml of diethyl ether with agitation. Water and ether level were separated. 500 ml of ether added to water level with agitation twice.

Ether was combined and recovered under reduced pressure and still residue was obtained. Hot water added to residue on steam bath for 30 min. Water solution was cooled and filtrated. Active carbon added to filtrate on steam bath. Active carbon was removed by filtration and filtrate was saved. Filtrate was heated to 100° C. and kept 10 min and filtrated at 85–90° C. Filtrate solution was concentrated under reduced pressure and cooled. The ether added to filtrate solution and kept at 0° C. for crystallized. The crystal was collected by filtration. Crystal dissolved in 30% of NaOH in steam bath. Solution was decolorized by active carbon. Water solution was concentrated under reduced pressure and crystallized at 0° C. White crystal was collected by filtration. Crystal dried under vacuum. The final product is resveratol.

EXAMPLE 2

Extraction of Resveratol from Plant Stem

Stem of plant was dried and powdered. The plant is peanut or Polygonum L or Arachis L or Leguminosae L. 1 kg dried powder of plant stem were extracted by 5L of 95% of ethanol. The powder was recovered by filtration. Filtrate was saved and powder filtercake was refluxed twice with 3 liter of 95% of ethanol on steam bath. Filtrates were combined and distilled at reduced pressure. The still residue was obtained. The still residue was extracted by 500 ml of water and 500 ml of diethyl ether with agitation. Water and ether level were separated. 500 ml of ether added to water level with agitation. Ether extractions were repeated five times. Ether was combined and recovered under reduced pressure and still residue was obtained. Hot water added to residue on steam bath for 30 min. Water solution was cooled and filtrated. Active carbon added to filtrate on steam bath. Filtrate was heated to 100° C. and kept 10 min and filtrated at 85–90° C. Water solution was concentrated under reduced pressure and cooled. The ether added to water solution and kept at 0° C. for crystallized. The crystal was collected by filtration. Crystal dissolved in 30% of MeOH in steam bath. Solution was decolorized by active carbon. Water solution was concentrated under reduced pressure and crystallized at 0° C. White crystal was collected by filtration. Crystal dried under vacuum. The final product is resveratol.

EXAMPLE 3

RES Injecting Preparation

RES, according to the conventional methods, was made as ampoules or other injection preparation, and then sterilized. Type XGI.S double door functional ampoule sterilizing machine is used for manufacturing of RES injection. The function of facilities includes sterilization, leakage detection and washing. Microcomputer (PC machine) is applied in the principal controlling system. Dose is intramuscularly 5–100 mg daily.

EXAMPLE 4

RES Oral Preparation

RES powder granulated accorded to the conventional granulation method. The mixture content decreased from 100% to 93%. The 7% of content was different types of fillers. Disintegrants and lubricants were used: microcrystalline cellulose (Avicel PH 105, PH 101, PH 102, PH 200, all from FMC Corp., Lehmann and Voss and Co., Hamburg, Germany; and Vivacel 200, Rettenmaier and Söhne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), α-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethyl cellulose (Ac-Di-Sol, FMC Corp./Lehmann and Voss and Co.; and Nymcel ZSB 10, Nymcel ZSB16, METSÄ-SERLA, Njimegen, Netherlands), Cross-linked calcium carboxymethyl-cellulose (ECG 505, FMC Corp./Lehmann and Voss and Co.), potato strach (Coeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etsu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany). Colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of RES was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-$\mu$m sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

The dosage of RES is orally 50–200 mg daily.

EXAMPLE 5

Effect of RES on GSH-Px

Glutathion peroxidase (GSH-Px) is an important enzyme, which has a high activity in cancer tissues.

Twenty animals were divided into two groups of ten each and fed with either normal drinking water (control group) or 0.2% of RES solution (experimental group); this defined feeding regimen was continued up to 30 days. At the end of the feeding regimen, the animals were sacrificed, and whole skin, small bowel, liver, and lung were removed and immediately placed in ice-cold 0.1 M phosphate buffer, pH 7.4. Tissues were cleaned properly, minced and homogenized in the same buffer, and a 100,000×g supernatant fraction was prepared as described earlier. GSH-Px and GSH-r activities were measured.

TABLE 1

Effect of RES on GSH-Px

| Group | GSH-Px activity (n mol NADPH oxidized/mg protein/min) | | |
|---|---|---|---|
| | Skin | Liver | Lung |
| Control | 205 ± 25 | 180 ± 2.0 | 9 ± 1.0 |
| Treatment | 260 ± 30* | 34 ± 50** | 22 ± 3.5** |

*P < 0.01 statistically significant compared with control group
**P < 0.001 statistically significant compared with control group Data of above table indicated that RES increases activities of GSH-Px in the skin, liver and lungs. It means that RES can prevent cancer in target tissues.

EXAMPLE 6

Effect of RES on Super-oxidation During Reperfusion of Ischemia Heart

A number of evidences indicated that superoxide anion, hydrogen superoxide, and hydroxyl radical were directive causes for ischemia or reperfusion damage. $H_2O_2$ in the body is cleared by catalase and glutathione peroxidase (GSH-Px) catalysis. In myocardium, catalase activity of GSH-Px was lower.

In the present study we examined the effect of RES on super-oxidation during reperfusion of ischemia heart.

Male rats (280 to 320 g body weight) of Spague-Dawley strain maintained on a standard diet were used in these experiments. The rats were lightly anesthetized with diethyl ether, the left femoral vein was exposed and heparin (200 IU) was administered intravenously. 1 minute after administration of heparin the heart was excised and placed in ice cool perfusion medium until contraction had ceased. The heart was then mounted on the perfusion apparatus.

Langendorff perfusion for an initial 10 min. period, the perfusion was continued as a working preparation for an additional 30 min. The hearts were all electrically paced at between 265 and 275 beats/min during working perfusion. This working load resulted in 60% to 75% of maximal, maintainable peak systolic pressure.

The perfusate was Krebs-Henseleit bicarbonate buffer gassed with 95% oxygen and 5% carbon dioxide. This perfusate contained 11 mM D-glucose during the Langendorff perfusion.

Aortic pressure, heart rates, coronary flows and aortic outputs were monitored during perfusion. The perfusate of treatment group contained 0.05 mg of RES /ml. The perfusate of control group contained buffer only. At the end the frozen hears were store in liquid nitrogen until assayed for metabolic intermediates.

The tissue sample was extracted in ice-cold 10% trichloroacetic acid and centrifuged at 10,000×g for 15 min. at 4° C. The precipitates of trichloroacetic acid were washed with 1% trichloroacetic acid and subsequently used for determining levels biochemical index of lactate. The data were expressed per gram of non-collagen protein (NCP).

SOD and GSH-Px were assayed.

The experimental data are listed in Table 2.

TABLE 2

Effect of RES on super-oxidation (1)

| Group | SOD activity ($\mu$g/protein) |
|---|---|
| Normal (N) | 11.0 ± 1.5 |
| Ischemia (C) | 7.0 ± 0.8* |
| Ischemia + RES (T) | 10.5 ± 1.2** |

*P < 0.01 as compared with N group;
**P < 0.00 1 as compared with C Group.

TABLE 3

Effect of RES on super-oxidation (2)

| Group | GSH-Px ($\mu$/g.w) |
|---|---|
| Normal (N) | 20.0 ± 2.5 |
| Ischemia (C) | 15.4 ± 1.5* |
| Ischemia + RES (T) | 18.9 ± 2.0** |

*P < 0.01 as compared with N group;
**P < 0.001 as compared with C Group.

This study indicated when myocardium ischemia, SOD activity was low. When ischemia 60 min, a large number of free radicals produced in myocardium. It is also known that product of free radicals was more obvious in reperfusion time.

With ischemia time extension, GSH-Px activity started to lower. When ischemia 60 min, it was more lower. Preperfusion with $4 \times 10^{-6}$ g of RES/ml, SOD and GSH-Px activities were significantly higher than those in control group. Data of Table 2 and 3 showed that RES could significantly reduce oxygen radical level of reperfusion ischemia heart.

EXAMPLE 7

Effect of RES on Peroxidation

It is known that RES can inhibit lipid peroxidation.

The experiments were performed as previously described. Hepatic lipoperoxide content was determined as described by Uchiyama.

In the present study, the effect of RES on lipoperoxides was examined.

TABLE 4

Effect of RES on peroxidation

| Group | Lipoperoxides (mmol MDA/g liver protein) | | | | |
| --- | --- | --- | --- | --- | --- |
| | 1 h | 3 h | 6 h | 12 h | 24 h |
| Control | 0.80 ± 0.09 | 0.90 ± 0.09 | 1.1 ± 1.0 | 1.3 ± 1.2 | 2.2 ± 2.0 |
| Treatment | 0.65 ± 0.07* | 0.62 ± 0.069** | 0.60 ± 0.70** | 0.59 ± 0.60** | 0.58 ± 0.58** |

*P < 0.05 compared with control group
**P < 0.01 compared with control group

It is known that the pathogenesis of $CCl_4$—induced hepatic damage involved reactive oxidant species increasing from the metabolism. The liver injure caused by $CCl_4$ is due to the formation of a reactive toxic metabolite by the hepatic cytochrome P-450 system. As data of Table 4 indicated that lipoperoxides are obviously increased in 1, 3, 6, 12 and 24 hours and RES decreases lipoperoxides significantly.

EXAMPLE 8

Effect of RES on Hepatic Microsomal Monooxygenases

As mentioned above section, the RES markedly decreased lipoperoxides. T/C was 87% (1h), 72% (3h), 55% (6h), 40% (12h) and 22% (24h). It means that RES could obviously protected injury, which caused by $CCl_4$.

In the present study, the effect of RES on the activities of hepatic microsomal monooxygenases was examined.

Microsomal preparations—the microsomes used were prepared from rat's liver. The liver was thoroughly perfused in situ with more than 200 ml of 0.9% NaCl solution. The liver was excised, and homogenized with 4 volumes of isotonic (1.15%) KCl solution in a Potter glass homogenizer. The homogenate was centrifuged at 12,000×g for 25 minutes in a refrigerated centrifuge, and the precipitate was discarded. The microsomes were sedimented by centrifugation at 78,000×g for 90 minutes in a Hitachi model 40P preparative ultracentrifuge. The firmly packed pellet of microsomes was resuspended in isotonic KCl solution with the Potter homogenizer and again centrifuged as above. The washed microsomes were finally suspended in isotonic KCl, usually at a concentration of 10 mg of protein per ml. The resultant microsomal suspensions were stored at 4° C. and used within 2 to 3 days. In these preparations isotonic KCl was employed, instead of the more usual 0.25 M sucrose, so as to minimize the adsorption of hemoglobin on microsomes. The microsomal preparations thus obtained were found to be practically free of adsorbed hemoglobin, when examined by zone electrophoresis.

Cytochrome P-450, NADPH-cytochrome creductase, aminoyrine demethylase and benzpyrene hydroxylase determined as previously described. Other methods are as same as above section.

The experimental data are shown as the following table.

TABLE 5

Effect of RES on monooxygenases

| Group | Cytochrome P-450 (nmol/mg protein) | NADPH-cytochrome Creductase (nmol/mg protein) | Aminopyrine demethylase (nmol HCHO/mg protein) | Benzpyrene hydroxylase (nmol/mg protein) |
| --- | --- | --- | --- | --- |
| Control | 1.20 ± 0.13 | 120.8 ± 13 | 80.5 ± 9.0 | 20.8 ± 22 |
| Treatment | 2.65 ± 0.35 | 198.5 ± 20 | 170.0 ± 18 | 48.9 ± 5.8 |

The data of Table 5 indicated that RES increased the hepatic microsomal P-450, NADPH-cytochrome C, reductase aminopyrine demethylase, and benzopyrene hydroxylase activities. Above results suggested that RES induced monooxygenases. It means that RES has a protective effect of acute hepatic injury.

EXAMPLE 9

Effect of RES on Lower Density Lipoprotein Oxidation

In the present study we reported the effect of RES on lower density lipoprotein oxidation. The endothelial cells cultured accordance with the methods as described previously [18]. Fresh human plasma was prepared and LDL was separated with a grads density centrifugation (63000 rpm, 2 h, 1.019<d<1.063). Nitrogen gas and 0.01 mol of PBS added to prevent LDL oxidation. LDL and the protein content measured accordance with the methods as described previously.

The cells were divided as control group (LDL $1\times10^{-4}$ mol/L) and treatment group (RES group LDL+100 µg RES/ml). Cell cultured plates were placed in 37° C., $CO_2$ incubated box to incubated for 24 h. Determination of malonyldialdehyde (MDA) was accordance with Foloik's method.

The data of Table 6 showed that the MDA level of RES group was lower than that in control group (P<0.01).

TABLE 6

Effects of RES on bovine aortic smooth muscle cell modified LDL

| Group | MDA (nmol/mg protein, x ± s) |
|---|---|
| Control | 4.50 ± 0.35 |
| Treatment | 2.75 ± 0.29* |

*$P < 0.001$ compared with control group.

It is known that lower density lipoprotein oxidation caused cardiovascular disease. Lipid peroxidation, for example, induced injury in cardiac cells and primary products of lipid peroxidation increased transport of calcium ions. Therefore, decreasing lower density lipoprotein oxidation could prevent and treat atherosclerosis. The data of Table 6 showed that RES could significantly decrease MDA. It means that RES could inhibit oxidative-modified LDL.

The inhibited effects of RES on cell oxidative-modified LDL could help explanation for RES treating atherosclerosis.

EXAMPLE 10

Effect of RES on Prevention of Epidermis Cancer

It is known that tetradecanoyphorbol-13-acetate (TPA) is strong tumor promoter and TPA can remarkable increase [$^3$H] thymidine incorporation in mouse epidermis and then to induce Epidermis cancer.

Mice were treated with TPA and the rate of [$^3$H] thymidine incorporation was determined 20 hours later. Male mice (7–9 weeks old) used for experiments. Only mice showing no hair regrowth following shaving were used. Animals were injected intraperitoneally (i.p.) with TPA or 95% saline. After 20 hours, mice were injected i.p. with 60 $\mu$Ci of [$^3$H] thymidine (2 Ci/mmol) 20 minutes before sacrifice. Epidermal scrapings were prepared. Homogenized in distilled water at 4° C., and the macromolecules precipitated with 0.4 N trichloracetic acid (TCA). Following 6 washes with 0.2 N TCA at 4° C. and 2 washes with absolute ethanol at room temperature, the nucleic acids were hydrolyzed with 0.5 N TCA at 90° C. for 5 minutes. The hydrolysates (0.2 ml aliquots) were counted in a scintillation counter and assayed for DNA. Each value is the mean±range for three separately treated mice. Each counted aliquot (0.2 ml) contained approximately 10 $\mu$g of DNA.

TABLE 7

Effect of RES on the rate of [$^3$H] thymidine incorporation in normal and TPA-stimulated mouse epidermis.

| | Specific activity (cpm/$\mu$g DNA) | |
|---|---|---|
| Treatment | Normal | TPA |
| Saline | 40.0 ± 0.8 | 120 ± 4.5 |
| RES | 32.2 ± 4.0 | 33.0 ± 4.5 |

Data of table 7 indicated that RES could remarkable inhibit DNA synthesis of TPA-stimulated mouse epidermis. Therefore, the experiments indicated that RES could prevent epidermis cancer.

EXAMPLE 11

Effect of RES on Tumor Suppressor of Gastric Cancer Cells

Gastric cancer is one of the most cancer diseases in the world. The recent progress made in molecular genetics has revealed that p53 gene is a tumor suppressor gene. Disorder of mutations of p53 plays a very important role in the development of many cancers. D17S5 hypermethylation, 17p allelic and p53 mutations appears to be the most common genetic abnormalities in cancer including in the development of gastric cancer. However, determinate tumor suppressor of gastric cancer cells is very difficult and experimental errors are lager. The present invention proved a new and easy method for determinate tumor suppressor of gastric cancer cells.

The gastric cancer cells and normal cells were cultured in RPMI 1640 medium supplement with 10% fetal bovine serum. All the exons of the $p^{53}$ gene were amplified by the polymease chain reaction (PCR) using specific oligonucleotide primers. The PCR products were subjected to single-strand conformation polymorphism (SSCP) analysis. A second PCR-SSCP analysis was performed to ensure that the results were reproducible in each experiment, which showed mobility. $p^{53}$ was determined.

TABLE 8

Effect of RES on $p^{53}$ allelic loss

| Group | Frequency of $p^{53}$ allelic loss (%) | Inhibition T/C (%) | P |
|---|---|---|---|
| Normal gastric cells | 0 | 0 | — |
| Gastric cancer cells (no drug) | 35 | — | — |
| Gastric cancer cells treated by RES | 12 | 36 | <0.01 |

TABLE 9

The effect of RES on $^{17}$p allelic loss

| Group | Frequency of $^{17}$p allelic loss (%) | Inhibition T/C (%) | P |
|---|---|---|---|
| Normal gastric cells | 0 | 0 | — |
| Gastric cancer cells (no drug) | 38 | — | — |
| Gastric cancer cells treated by RES | 18.8 | 49 | <0.01 |

A combination of different molecular genetic analysis is a highly sensitive method for analysis of genetic abnormalities. Data of table 8 and 9 showed that RES could obviously inhibit levels of DNA methylation and $p^{53}$ mutations and $^{17}$p allelic loss of cancer cells. Table 9 showed that RES could increase function of tumor suppressor. Molecular genetics has revealed that increased tumor suppressor can treat and prevent cancer.

EXAMPLE 12

The Effect of RES on Control of Oncogenes

Human myeloblastic leukemic cell (ML-1) had been described previously. Cells were maintained in suspension culture in RPMI 1640 medium supplemented with 7.5% heat-inactivated FBS. Cells growth and viability were assayed by hemocytometer using trypan blue dye exclusion.

RNA was isolated by the CsCl gradient modification. RNA pellets were washed twice by reprecipitation in ethanol and quantitated by absorbency at 260 nM. RNA analyzed by electrophoresis of 15 $\mu$g of RNA through 1.2% agarose formaldehyde gels followed by northern blot transfer to nitrocellulose.

Single-standard uniformly labeled DNA probes were prepared. Probe of c-myc was a 1.7 Kb cla-Eco RI restriction fragment containing the 3'exon region of human c-myc and probe of c-myb was 1.0 Kb myb-specific Bam HI fragment. Probes for n-ras contained DNA fragments using a modification of the PCR technique. Probes for myb, myc and n-ras were isolated by electrolution. The isolated fragments were labeled to high specific activity with [$\alpha^{32}$P]-dCTP (3000 ci/mmol). Prehybridization of the filter was performed. The hybridization mixer contained 50,000 cpm of probe. The probes were hybridized at 58° C. in 15 mM NaCl, 1.5 nM sodium citrate for 3 hours. After hybridization, they were exposed to XAR-5 film. Oncogene expression was quantitated by densitometer scanning of the autoradiography.

The results are summarized in the tables as below.

TABLE 10

The effect of RES on inhibition of oncogenes

| Compound | Inhibition (%) | | | |
|---|---|---|---|---|
| (ng/ml) | c-myb RNA | c-myc RNA | n-ras RNA | P |
| Cultured medium | 0 | 0 | 0 | — |
| Saline | 0 | 0 | 0 | — |
| RES | 25.6 ± 3.5 | 30.1 ± 4.2 | 35.7 ± 3.8 | <0.01 |

The results presented above clearly suggested that RES has a significant effect of inhibiting oncogenes.

EXAMPLE 13

RES Inhibited Tumor Incidence in Vivo

The capacity of tobacco-specific nitrosamine 4-(methylnitrosamino)-1-(3-pyridyl)-1-butanone (NNK) to induce tumor incidence was recognized several years ago. Every group had 20 mice. For treatment group, each mouse was gave RES by injection at dose of 20 mg/kg daily. For control group, each mouse was gave same volume of physiological saline. Three days later, mice were gave 10 μmol NNK (in 0.1 ml saline) by i.p. injection. Sixteen weeks after these treatments the mice were killed and pulmonary adenomas were counted. The statistical significance of bioassay data was determined by student's test.

TABLE 11

Effect of RES on NNK-induced lung tumorigenesis

| Group | Tumor incidence (%) | P |
|---|---|---|
| Control | 100 | — |
| RES | 28.5 ± 3.0 | <0.01 |

Data of Table 11 indicated that RES has a significant inhibitory effect against lung tumor. RES can decrease tumor incidence. Therefore, RES can prevent cancer.

The preparation of drugs, which can be accomplished by the extraction methods set forth above or any conventional methods for extracting the active principles from the plants. The novelty of the present invention resides in the mixture of the active principles in the specified proportions to produce drugs, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of drugs concentration.

In addition, the present invention provides novel methods for treating and preventing a variety of cancer conditions and control cancer cells with produced safe pharmaceutical agent.

It will thus be shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed is:

1. A process for producing resveratrol in the form of dried white crystals from peanut oil residue and/or from peanut stems comprising:

(a) extracting a ground dried powder of the peanut oil residue and/or the peanut stems with 95% ethanol to obtain a crude extract;

(b) mixing and filtering the crude extract to obtain a filtercake and filtrate;

(c) refluxing the filtercake twice with 95% ethanol in a steam bath to obtain a refluxed extract;

(d) concentrating the filtrate obtained in step (b) and the refluxed extract obtained in step (c) under reduced pressure, and recovering the ethanol and still residue therefrom;

(e) extracting the still residue with a mixture of water and ethyl ether;

(f) separating and recovering the ethyl ether and still residue from step (e);

(g) adding hot water to the still residue obtained in step (f) in a steam bath to form a suspension;

(h) cooling and filtering the suspension to obtain a filtrate;

(i) adding active carbon to the filtrate obtained in step (h) in a steam bath with agitation;

(j) removing the active carbon by filtration to obtain a filtrate;

(k) concentrating the filtrate obtained in step (j) under reduced pressure, and cooling the concentrated filtrate;

(l) crystallizing the concentrated filtrate by adding ethyl ether to the concentrated filtrate to obtain crystals;

(m) collecting the crystals by filtration;

(n) dissolving the crystals in 30% NaOH to form a solution;

(o) decolorizing the solution by contacting the solution with active carbon;

(p) concentrating the decolorized solution under reduced pressure to obtain white crystals;

(q) collecting the white crystals by filtration; and (r) drying the white crystals under vacuum.

* * * * *